United States Patent [19]

Maddison et al.

[11] Patent Number: 5,330,520
[45] Date of Patent: Jul. 19, 1994

[54] IMPLANTABLE ELECTRODE AND SENSOR LEAD APPARATUS

[75] Inventors: David S. Maddison, Wollstonecraft; Michael Skalsky, Waverley; Gerhard Gotthardt, Castle Hill; Neil Anderson, Artarmon, all of Australia

[73] Assignee: Telectronics Pacing Systems, Inc., Englewood, Colo.

[21] Appl. No.: 772,975

[22] Filed: Oct. 8, 1991

Related U.S. Application Data

[63] Continuation-in-part of Ser. No. 617,949, Nov. 27, 1990, abandoned, and a continuation-in-part of Ser. No. 644,426, Jan. 22, 1991, abandoned, said Ser. No. 617,949, is a continuation of Ser. No. 453,125, Dec. 5, 1989, abandoned, which is a continuation of Ser. No. 223,738, Jul. 25, 1988, abandoned, which is a continuation of Ser. No. 863,357, May 15, 1986, abandoned, said Ser. No. 644,426, is a continuation of Ser. No. 188,487, Apr. 29, 1988, abandoned.

[51] Int. Cl.⁵ .............................................. A61N 1/05
[52] U.S. Cl. ..................................................... 607/122
[58] Field of Search .............................. 128/784–786, 128/419 P; 607/122, 123, 125–128

[56] References Cited

U.S. PATENT DOCUMENTS

| 4,033,357 | 7/1977 | Helland et al. ...................... 128/785 |
| 4,352,360 | 10/1982 | King .................................... 128/786 |
| 4,585,013 | 4/1986 | Harris ................................... 128/785 |
| 4,624,261 | 11/1986 | Holscher .............................. 128/635 |
| 4,784,161 | 11/1988 | Skalsky et al. ...................... 128/785 |

FOREIGN PATENT DOCUMENTS

| 0057450 | 8/1982 | European Pat. Off. ............ 128/785 |
| 2604581 | 8/1973 | Fed. Rep. of Germany ... 128/419 P |
| 2822829 | 11/1979 | Fed. Rep. of Germany ...... 128/786 |

OTHER PUBLICATIONS

"New Plastics" *Newsweek*, pp. 77–78, Jun. 18, 1979.
Foos et al, "Conductive Polymer Electrodes for Neural Prosthetic Applications", Norwood, Mass.

*Primary Examiner*—Lee S. Cohen
*Attorney, Agent, or Firm*—Gottlieb, Rackman & Reisman

[57] ABSTRACT

A transvenous cardioversion lead system capable of delivering electrical energy to cardiac tissue is provided. Lead system comprises an inner conductor surrounded by an insulative layer which, in turn, is surrounded by a second conductor mounted coaxially with the inner conductor. At least a portion of the second conductor is surrounded by an outer conductive sheath formed from a suitable material having an non-abrasive affect. This prevents damage to cardiac tissue during normal transvenous operating position while at the same time preventing thrombogenesis on the lead surface.

2 Claims, 11 Drawing Sheets

IMPLANTABLE ELECTRODE AND SENSOR LEAD APPARATUS

CROSS-REFERENCE TO RELATED APPLICATIONS

This application is a continuation-in-part of both U.S. patent application Ser. No. 07/617,949, filed Nov. 27, 1990, now abandoned, and U.S. patent application Ser. No. 07/644,426, filed Jan. 22, 1991, now abandoned. Ser. No. 07/617,949 is a continuation of U.S. patent application Ser. No. 07/453,125, filed Dec. 5, 1989, now abandoned, which is a continuation of U.S. patent application Ser. No. 07/223,738, filed Jul. 25, 1988, now abandoned, which was a continuation of U.S. patent application Ser. No. 06/863,357, filed May 15, 1986, now abandoned. Ser. No. 07/644,426 is a continuation of U.S. patent application Ser. No. 07/188,487, filed Apr. 29, 1988, now abandoned.

BACKGROUND OF THE INVENTION

1. Field of the Invention

This invention relates to a device for implantation in the human body that acts as a conductor of electricity for stimulating tissue and for sensing bio-electric activity emanating from the tissue. This invention especially relates to artificial cardiac pacemakers, but may be utilized with other devices requiring electrical conductors and stimulating electrodes within the body such as artificial implantable defibrillators, neuro stimulators, muscle stimulators, cochlear implants, and other devices.

2. Description of the Related Art

Cardiac pacemakers typically consist of two major portions. The first portion is the pulse generator which consists of a power source and electronics associated with producing electrical pulses, and the second portion consists of electrode leads for applying the generated pulses to body tissues. Conventional electrode leads typically consist of three primary parts. They include a lead body which provides a path for electrical conduction from the pulse generator to the body tissues, a proximal connector which connects the lead body to the pulse generator, and a distal electrode which delivers the electrical impulses to the body tissue. Common electrode leads are either unipolar (one electrode) or bipolar (two electrodes). Multipolar leads (more than two electrodes) are needed for use with chronic heart patients, and a number of conductors may also be desired for sensory inputs to measure such factors as oxygen concentration, temperature, blood flow or pressure and motion detection. Such multiple conductor leads are impractical with current technology however, because the many conductors needed cause the electrode lead diameter to become excessive. Similarly, the multiple leads required for sensor inputs are not practical under current technology because the electrode lead diameter becomes excessive.

Further problems with multiple electrode leads are caused by the bulky connector constructions that are conventionally used. Conductors are typically connected by mechanical means which require additional components such as crimping support pins or tubes. These connectors add to the size and weight of the implants and reduce lead flexibility, particularly as the number of conductors increases.

Currently used implantable leads consist of an electrical conductor with a layer of electrical insulation. The conductor may be in the form of a straight metal wire or a helical coil. Solid wires, however, are prone to fracture from fatigue caused by bending stresses associated with body implants. Metal coils have higher fatigue resistance, but their bulkier construction reduces design flexibility. Conductors made of platinum and stainless steel were originally used for such applications, but their high cost or relatively poor corrosion resistance led to the development of more fatigue-resistant alloys and composites, including those sold under the trademarks "MP35N" and "ELGILOY," and silver/stainless steel composite materials. More recent developments have included multifilar tensile wires, and designs incorporating carbon (graphite) fiber or tungsten as a conductor have been proposed. Materials for insulating these conductors include silicone rubber, polyurethane, and other insulating materials, such as that sold under the trademark "TEFLON."

There have been several attempts at integrating the conductor and insulator by using conductor wires that are wrapped helically around an insulator core and then encapsulated by a second insulating layer. These are disclosed in U.S. Pat. No. 3,760,812 issued to Timm et al., U.S. Pat. Nos. 3,485,234, 3,585,707 issued to Stevens, and International patent application No. PCT/U583/00827 to Berkley. However, these integral metal electrode leads suffer from many of the aforementioned drawbacks that are associated with all metal conductor/polymer insulator systems.

The use of metallic conductors with a separate insulator and mechanical means for connecting the conductors to electrodes or pulse generating mechanisms have a number of disadvantages. The following problems are associated with such devices:

1. It is difficult and expensive (i.e., labor intensive) to terminate electrode leads of conventional design due to the fact that the alloys utilized cannot be readily welded or bonded. Also, the helically coiled conductors are expensive to wind and they require precision equipment and a great deal of process control during manufacture.

2. Metals generally are relatively dense compared with the density of body tissues and thus cause mechanical irritation to body tissues.

3. Although metals presently used in electrode leads are selected for their high corrosion resistance, the possibility of corrosion cannot be entirely eliminated when there are metal-to-metal connections.

4. Metals generally have a finite fatigue life so that designing electrode leads for long-term performance often limits design possibilities because of reduced conductivity and increased size.

5. Design flexibility with currently used electrode leads is further limited by the sizable helix diameter required for fatigue resistance and by the insulation thickness dictated by safety requirements.

6. With present technology, it is impractical to design an electrode lead in which a distal stimulating tip and a proximal end connector are an integral part of the design.

7. Multipolar conductors according to present technology require excessively large leads that have significantly reduced flexibility.

SUMMARY OF THE INVENTION

Accordingly, it is an object of the invention to provide a body implantable electrode lead apparatus characterized by a low density and by superior corrosion and fatigue resistance, that is also acceptable to the body.

It is another object of the present invention to provide an electrode lead apparatus with an integral proximal end connector and an integral distal end electrode.

It is still another object of the present invention to provide an electrode lead apparatus that is compact even with multipolar conductors.

Still another object of the invention is to prevent damage occurring to the heart tissue and tricuspid value during the motion of heart contraction while maintaining a large electrode surface area.

Another object of the invention is to reduce the risk of thrombogenesis and emboli.

Additional objects and advantages of the present invention will be set forth in part in the description that follows and in part will be obvious from the description or may be learned by practice of the invention. The objects and advantages of the invention may be realized and obtained by the methods and apparatus particularly pointed out in the appended claims.

To achieve the objects and in accordance with the purpose of the invention, as embodied and as broadly described herein, the present invention provides a body implantable electrode lead apparatus for delivering electric pulses from an electrical pulse generator to body tissues, and comprises: an electrical conductor comprised of a polymeric material and having a proximal end and a distal end; means for insulating the electrical conductor; means for coupling the proximal end of the electrical conductor to the electric pulse generator; and an electrode for delivering electrical pulses from the distal end of the conductor to the body tissues. A sensory element may be coupled to the electrical conductor in the region proximate the distal tip.

The accompanying drawings, which are incorporated in and constitute a part of this specification, illustrate presently preferred embodiments of the invention and, together with the description, serve to explain the principles of the invention.

DESCRIPTION OF THE PREFERRED EMBODIMENTS

Figure 1:
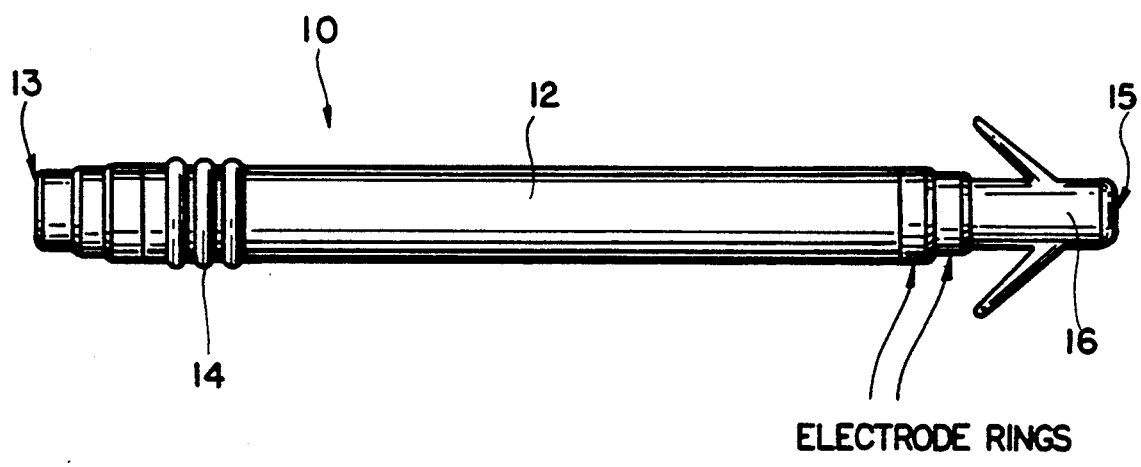
FIG. 1 shows an electrode lead comprising one embodiment of the present invention.

Reference will now be made in detail to the present preferred embodiments of the invention, examples of which are illustrated in the accompanying drawings. Throughout the drawings, like reference characters are used to designate like elements.

In FIG. 1, an electrode lead apparatus 10 according to this invention is illustrated. The electrode lead apparatus, generally designated 10, delivers electrical pulses from an electrical pulse generator to body tissues. The electric pulse generator (not shown) may comprise a cardiac pacemaker, implantable defibrillator, neurostimulator, muscle stimulator, cochlear implant or other device depending upon the type of electrical stimulation required.

According to the present invention, an electrical conductor is provided with two ends, a proximal end 13 and a distal end 15. A proximal connector 14 is located at the proximal end of the conductor while a distal tip 16 is located at the distal end of the electrical conductor.

As embodied herein the electrical conductor is comprised of a polymeric material. Because conventional materials for producing conductors do not possess the appropriate properties for the construction of human body implantable electrode leads, this invention uses novel materials in a novel way to produce an electrode lead with the requisite properties.

It is preferable for implantable electrode lead polymers to be at least as fatigue resistant as presently utilized pacemaker leads. A fatigue resistance of $200 \times 10^3$ cycles when flexed around a 4 mm radius is preferred. Fatigue resistance in conductive polypyrroles has been improved by the addition of toughening additives.

It is further preferred that polymers utilized in body implantable electrode leads be biocompatible. The optimum polymers should be inert to oxygen and water as is the case with many conductive polymers.

Examples of a suitable conductive polymer are polymers filled with a conductive medium such as silver, carbon (graphite) or titanium flakes or powder which render the composite medium conductive. Alternately, such conducting polymers can be created by thin film (e.g., sputtering or PCB technology) deposition of metal onto a polymer. These polymeric composite conductors are well-known in the art and need not be described in further detail herein for purposes of the present invention.

In an alternative embodiment, polymers which are intrinsically conductive due to the electronic structure of the polymer molecules may comprise the electrical conductor. Polymers with conductivities between $10^3$ and $10^4$ $(ohm\ cm)^{-1}$ are preferable for use in electrode leads having conductor diameters between 0.1 and 0.4 mm. For a larger 0.6 mm diameter electrode lead, a polymer with a conductivity of $10^2\ (ohm\ cm)^{-1}$ is sufficient. Poly(sulphur nitride) and doped polyacetylene polymers are known to have conductivities in the $10^3$ to $10^4\ (ohm\ cm)^{-1}$ range.

Intrinsically conductive polymers are described in a paper by R. J. Young entitled "Conducting Polymers," presented at the Australian RACI Polymer Division Symposium on Electrical, Optical and Acoustic Properties of Polymers and in an article by the same author entitled "Conducting Polymers—Plastic Metals?", 9 Plastics and Rubber International, 29 (February 1984), both of which are expressly incorporated herein by reference. Intrinsically conductive polymers may include, but are not limited to, polyacetylene, polypyrrole, poly(para-phenylene), poly(paraphenylene sulfide), poly(sulphur nitride) and polymers whose conductivity is increased by "doping" with certain molecules or lions. Polyacetylene is synthesized by blowing acetylene gas onto the surface of a catalyst solution of a mixture of triethyl aluminum and titanium tetrabutoxide, while polypyrrole is synthesized from a solution containing pyrrole, tetraethylammonium toluenesulfonate and acetonitrile. The above ingredients are commercially available and Polaroid Corp. is presently marketing polypyrrole for experimental evaluation.

Polymers "doped" with electron accepting molecules such as iodine, bromine and arsenic pentafluoride or electron donors such as alkali metals exhibit substantially increased Conductivity. Substantial quantities of dopant, in the concentration range of 1-8%, are included in the polymers to obtain the desired conductivity increases. These conductive polymers, when applied in the novel electrode lead configurations described below, result in an electrode lead with those properties required for body implantation.

According to the invention, means for insulating the electrical conductor is provided. As embodied herein, the means for insulating comprise insulating materials including polyurethane, silicone or other biocompatible materials. The insulating means must also be compatible with polymer material. Biocompatible electrical insulating materials suitable for these purposes are well-known in the art and need not be described in further detail.

Figure 2A:
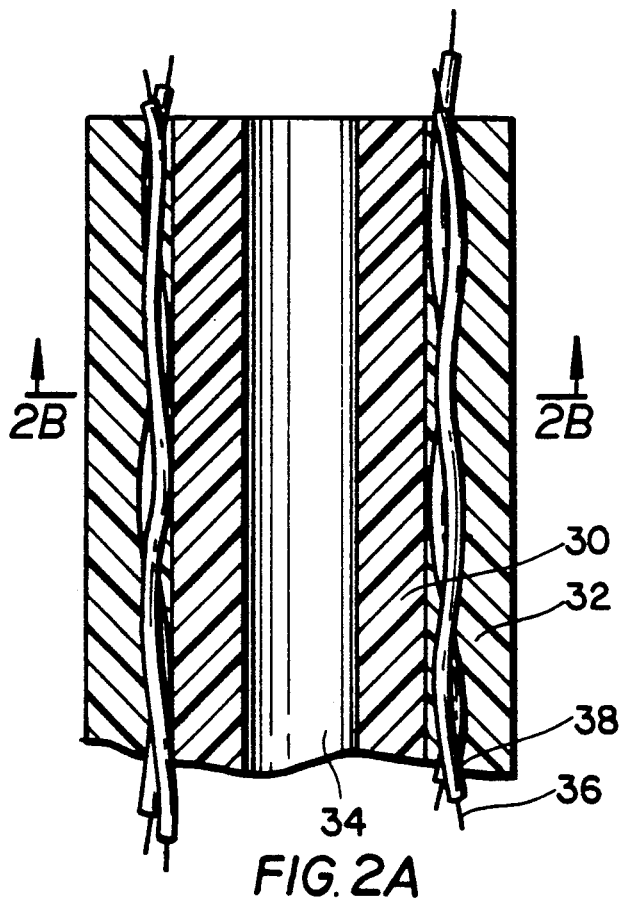
FIG. 2(a) is a sectional side view of an electrode lead according to one embodiment of the present invention in which the conductors are additionally imbedded in an insulator material.
Figure 2C:
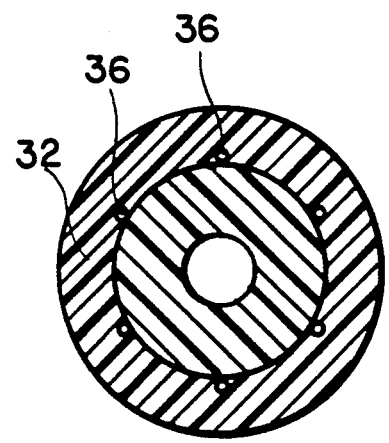
FIG. 2(c) is a cross-sectional view of another embodiment of the electrode lead shown in FIG. 2(a)
Figure 2D:
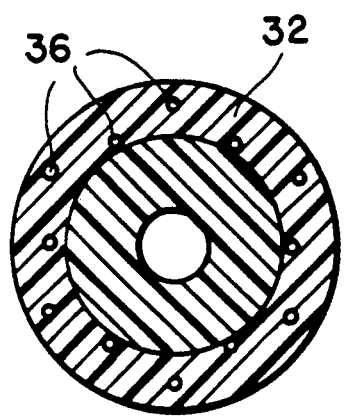
FIG. 2(d) is a cross-sectional view of another embodiment of the electrode lead shown in FIG. 2(a)
Figure 2B:
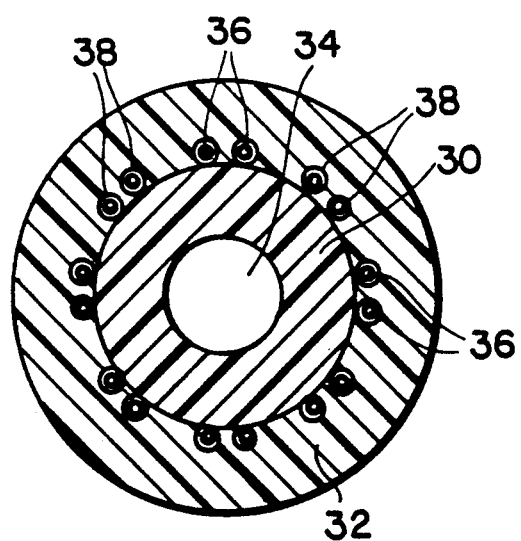
FIG. 2(b) is a cross-sectional view of the electrode lead of FIG. 2(a) taken along line 2b—2b.
Figure 2E:
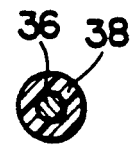
FIG. 2(e) is a cross-sectional view of an individual electrode lead.

FIGS. 2(a)-(e) illustrate a preferred electrode lead body configuration in which individual conductive polymer leads 36 are surrounded by insulating means comprising insulators 38. As shown in FIG. 2(b), the insulated conductive leads 36 surround a first insulating layer 30 having a stylet hole 34. The individually encased conductive leads 36 may be arranged in groups of two or more, as illustrated in FIG. 2(b), or they may be individually distributed, as illustrated in FIGS. 2(c) and 2(d). When grouped, the leads may be aligned parallel with each other or they may be twisted with each other.

A second insulating layer 32 coaxially surrounds the first insulating layer 30 and also encases the individually encased conductive leads 36. Alternatively, as shown in FIGS. 2(c) and 2(d), the electrical conductors 36 may be directly encased in the second insulating layer 32. Where an application requires many conductors in a small area, the electrode lead of FIG. 2(b), which will accommodate a large number of conductors within a relatively small cross sectional area, is preferred. However, the application of an individual insulating layer 38 to each of the conductors 36 in the electrode lead of FIG. 2(b) requires increased handling during manufacture. Where fewer conductors or a less compact lead is required, the leads shown in FIGS. 2(c) and 2(d), which are more economical to produce than the lead of FIG. 2(b), may be preferable.

Figure 3A:
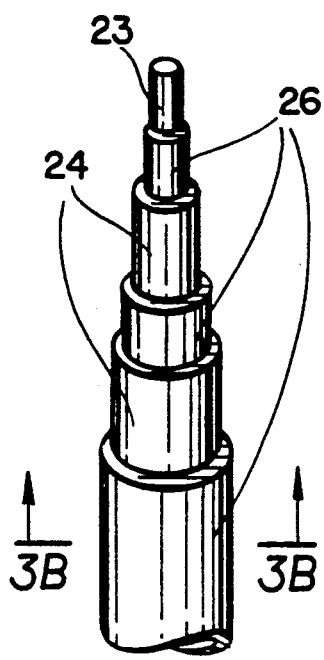
FIG. 3(a) is a perspective view of an exposed end of an electrical conductor lead according to the present invention in which the conductors are arranged coaxially.
Figure 3B:
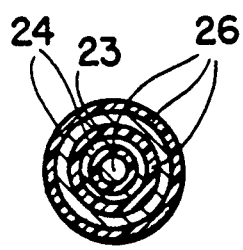
FIG. 3(b) is a cross-sectional view of the conductor shown in FIG. 3(a) taken along line 3b—3b.

In an alternative embodiment as illustrated in FIGS. 3(a) and 3(b), a conductive polymer lead 23 is coaxially surrounded by additional hollow conductive polymer leads 24 with insulator layers 26 formed between each conductive polymer lead.

Figure 4:
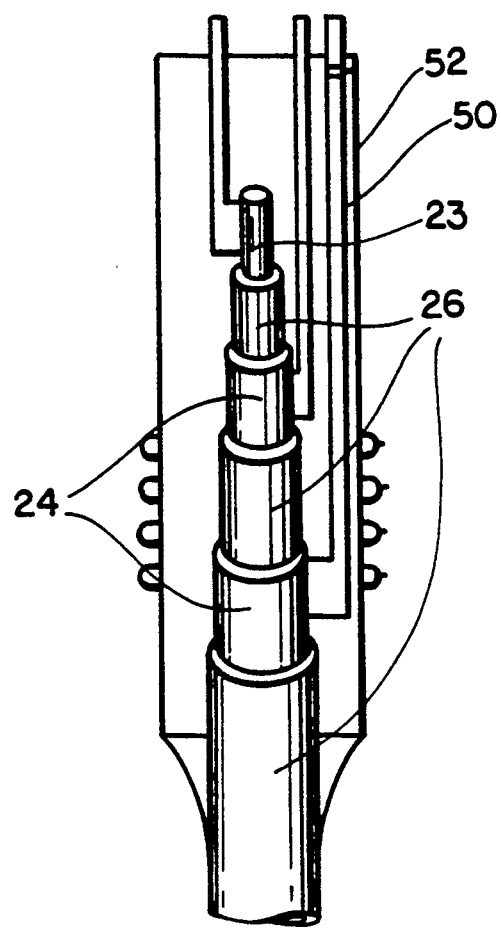
FIG. 4 is a perspective view of the end of the electrode lead of FIG. 3 in which the coaxial conductors are stepped and coupled to terminal connector shims.

According to the invention, means are also provided for coupling the proximal end of the electrical conductor to the electrical pulse generator. As embodied herein, the electrode lead 12 may be provided with a variety of coupling structures. In FIG. 4, a coupling structure for the proximal end of the coaxial style electrode lead of FIG. 3 is shown. FIG. 4 illustrates a three conductor device, but the principle shown and described is applicable for one or more conductors. In FIG. 4, the coaxial electrode lead conductors 23, 24 and respective insulators 26 are cut down to create a stepped shape. Molded silicone or other material is molded into a silastic body 52 which fits over the stepped conductor lead distal tip. Incorporated in the silastic body are metal shims 50 which provide an electrical contact with respective ones of the coaxial conductive leads 23, 24. The metal 50 shims may be roughened or perforated to improve their contact with their respective conductors. This contact may be further improved by attaching shims 50 to the conductors with a conductive polymer adhesive.

In another embodiment, shims 50 are formed by filling corresponding hollow runs in the silastic body with conductive polymer which can be utilized to perform the same function as the metal shims 50. A coupling arrangement with shims is also applicable to the distal end of electrode leads with multiple conductors for connecting electrode leads to a stimulation electrode or a sensor.

Figure 6:
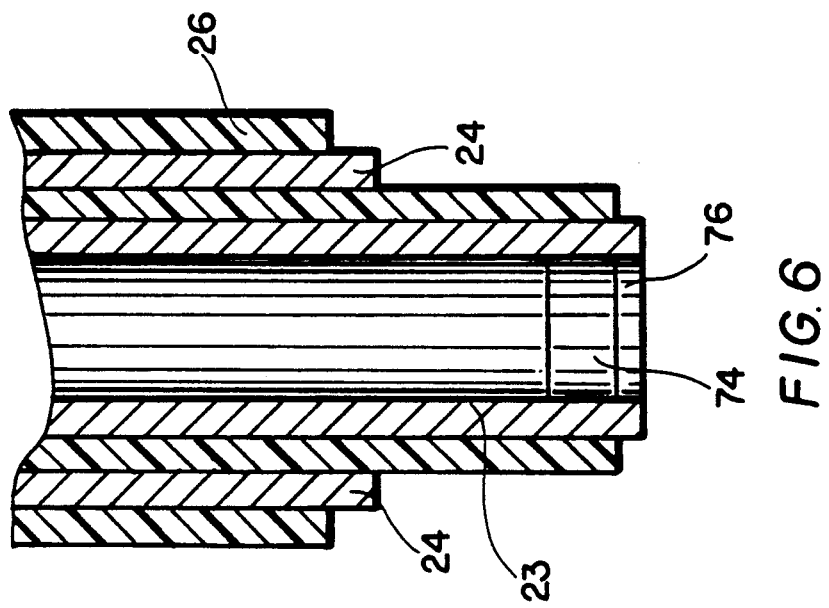
FIG. 6 is a side sectional view of another embodiment of the distal electrode lead tip of FIG. 5.
Figure 5:
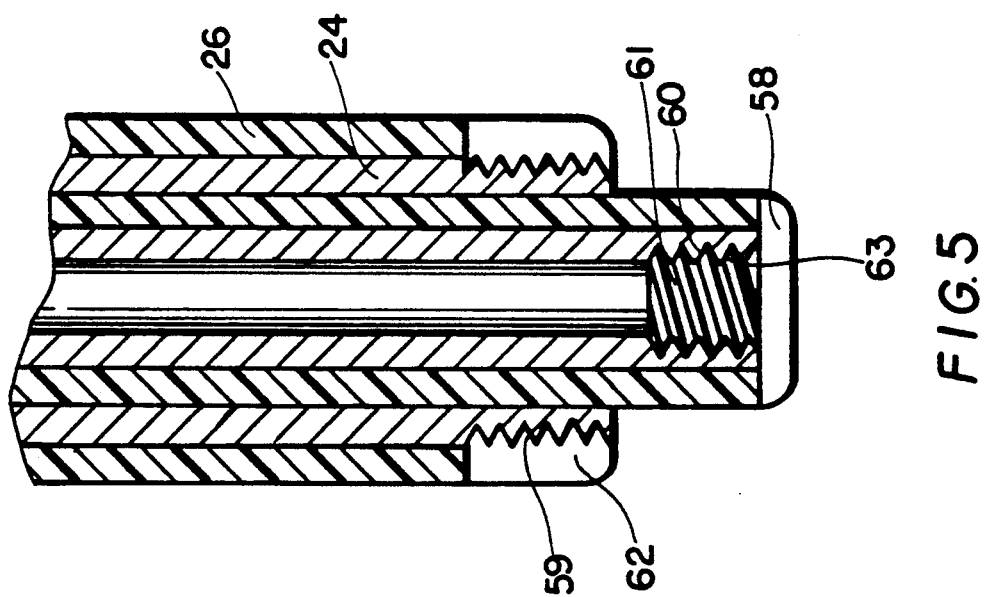
FIG. 5 is a side sectional view of the distal end of the electrode lead of FIG. 3.
Figure 7:
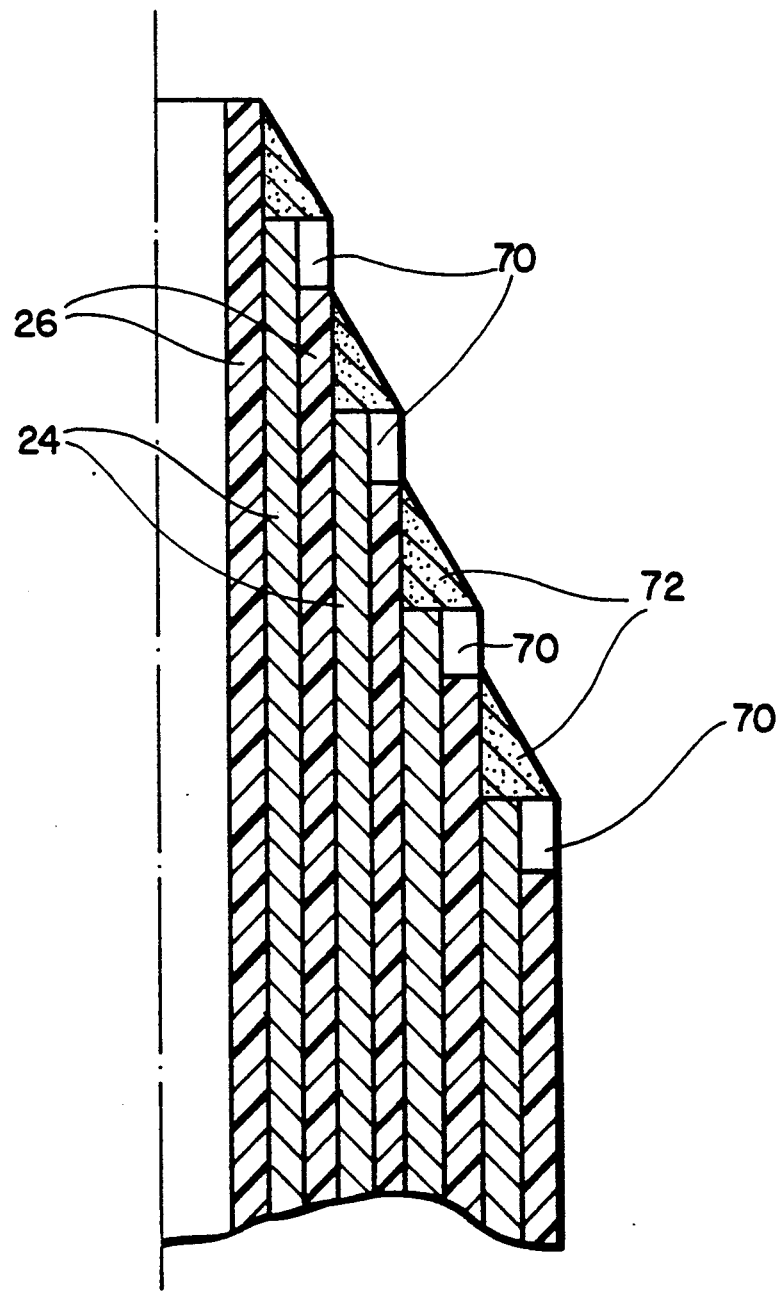
FIG. 7 is a partial side sectional view of another embodiment of the distal end of the electrode lead of FIG. 3.

According to the invention, electrode means for delivering the electrical pulses from the distal end of the conductor to the body tissues are provided. As embodied herein, the electrode means may comprise any one of a variety of structures as illustrated in FIGS. 5-7. FIG. 5 illustrates a stimulation electrode 58 fixed to the distal end of the electrode lead 12. The distal end of the electrode lead 12 has a coaxial hollow portion 61 that has interior threads or teeth 60. The distal electrode tip 58 includes a male portion with threads or teeth 63 that fit into the distal end of the electrode lead 12 to mate with the corresponding interior teeth or threads 60. Electrode ring 62 with interior threads or teeth 59 is similarly joined to the stepped end of conductive lead 24.

FIG. 6 illustrates the distal end of another embodiment of the electrode means which is fabricated without mechanical joining technology. The electrode tip 76 is fixed to or a part of a sealing plug 74 comprised of a biocompatible rigid or elastomer material such as silicon rubber, delrin of polyurethane. The tip 76 is attached to the conductive lead 23 by means of a conductive adhesive comprised of carbon or metal filled silicone rubber, epoxy or cyanoacrylate, or of an intrinsically conductive adhesive made with a conducting polymer. The end of the coaxial conductive lead 24 is exposed on the stepped distal end of the electrode lead 12 such that the end of the conductive lead 24 forms another exposed electrode.

As illustrated in FIG. 7, a plurality of separate electrode rings 70 may be slipped over the stepped end of the distal tip of electrode lead 12 to form rings that can act as sensors or electrodes. The rings 70 are individually bonded to respective ends of the stepped conductive leads by means of conductive adhesive 72 which also substantially fills in the discontinuities of the stepped conductor to give the end a generally smooth finish. The conductive adhesive 72 is also comprised of carbon or metal filled silicone rubber, epoxy or cyanoacrylate, or of an intrinsically conductive adhesive made with a conducting polymer. This structure is especially useful in a multipolar lead.

Figure 8:
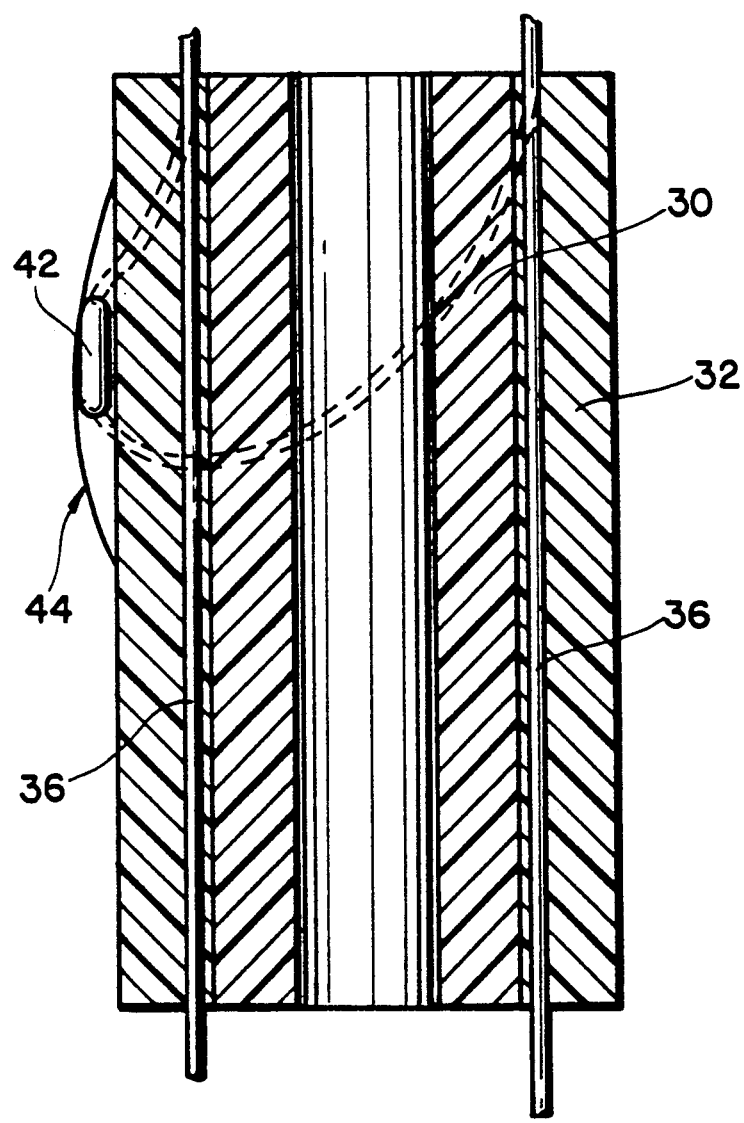
FIG. 8 is a side sectional view of the electrode lead of FIG. 2 showing a sensor attached to the conductors.

According to the present invention, sensory means for sensing temperature, pressure or oxygen concentration in a region proximate to the distal end of the electrical conductor may be provided. As embodied herein, the sensory means may comprise a sensor element proximate to the distal end of the electrode lead The sensor element may, for example, be a transistor type biosensor, or a piezoelectric detector for motion volume or pressure. With respect to the preferred embodiment, FIG. 8 shows a configuration in which sensor element 42 is attached to two of the conductive leads 36 and covered by an encapsulant 44. The encapsulant may be made of the same materials that comprise the insulators such as epoxy, polyurethane or silicone polymers. The distal end of the electrode lead 12 of the alternative embodiment illustrated in FIG. 3(a) may be similarly provided with sensor elements.

Figure 9:
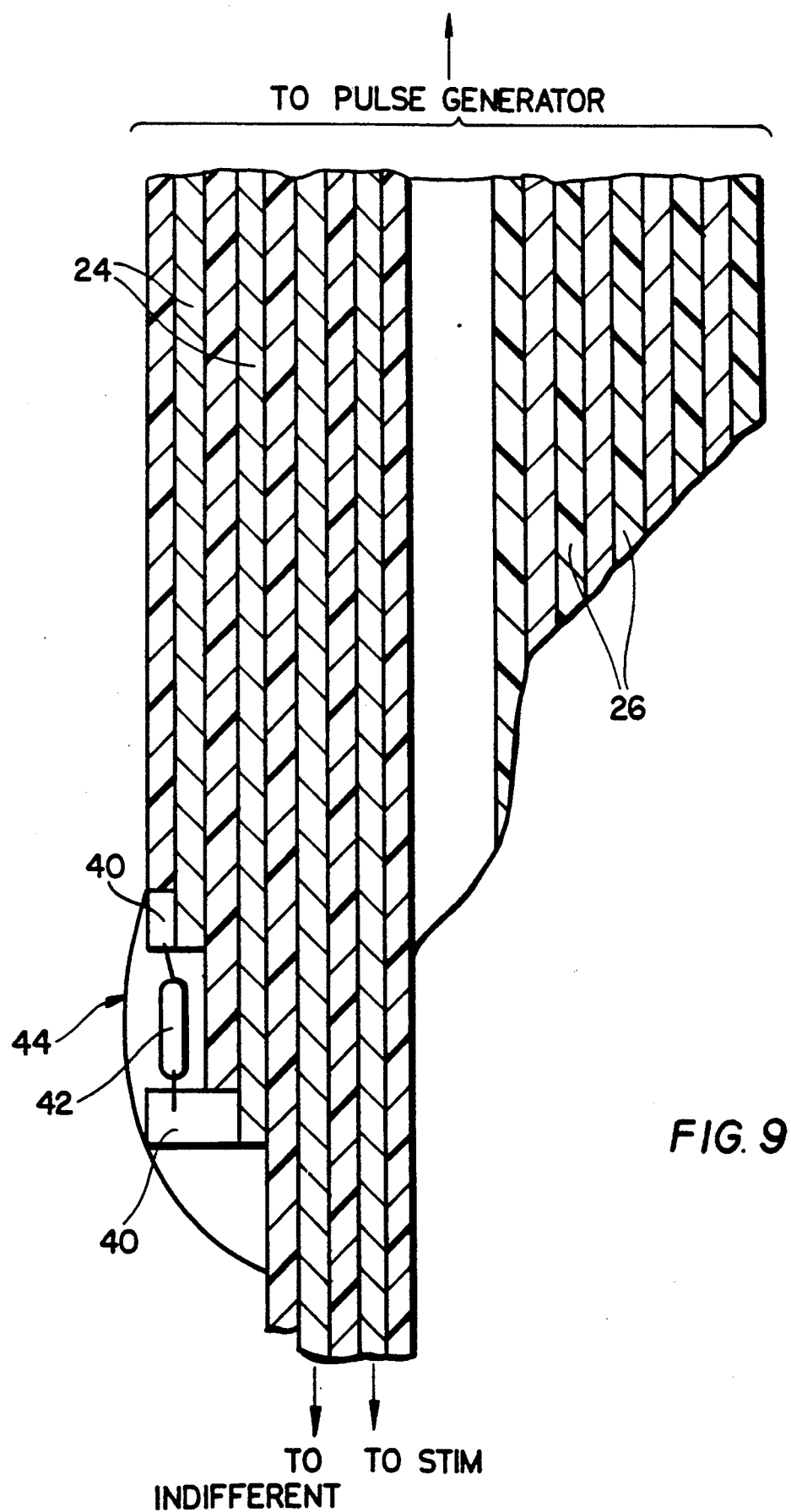
FIG. 9 is a partial cross-sectional view of the coaxial electrode lead of FIG. 3 showing a sensor attached to the coaxial conductors.

FIG. 9 illustrates individual concentric rings 40 surrounding and attached to the ends of several of the coaxial conductor leads 24. A sensor 42 is attached between two of the concentric rings 40 after which the concentric rings 40 and the sensor 42 are embedded in an encapsulant 44.

Figures 10, 10A:
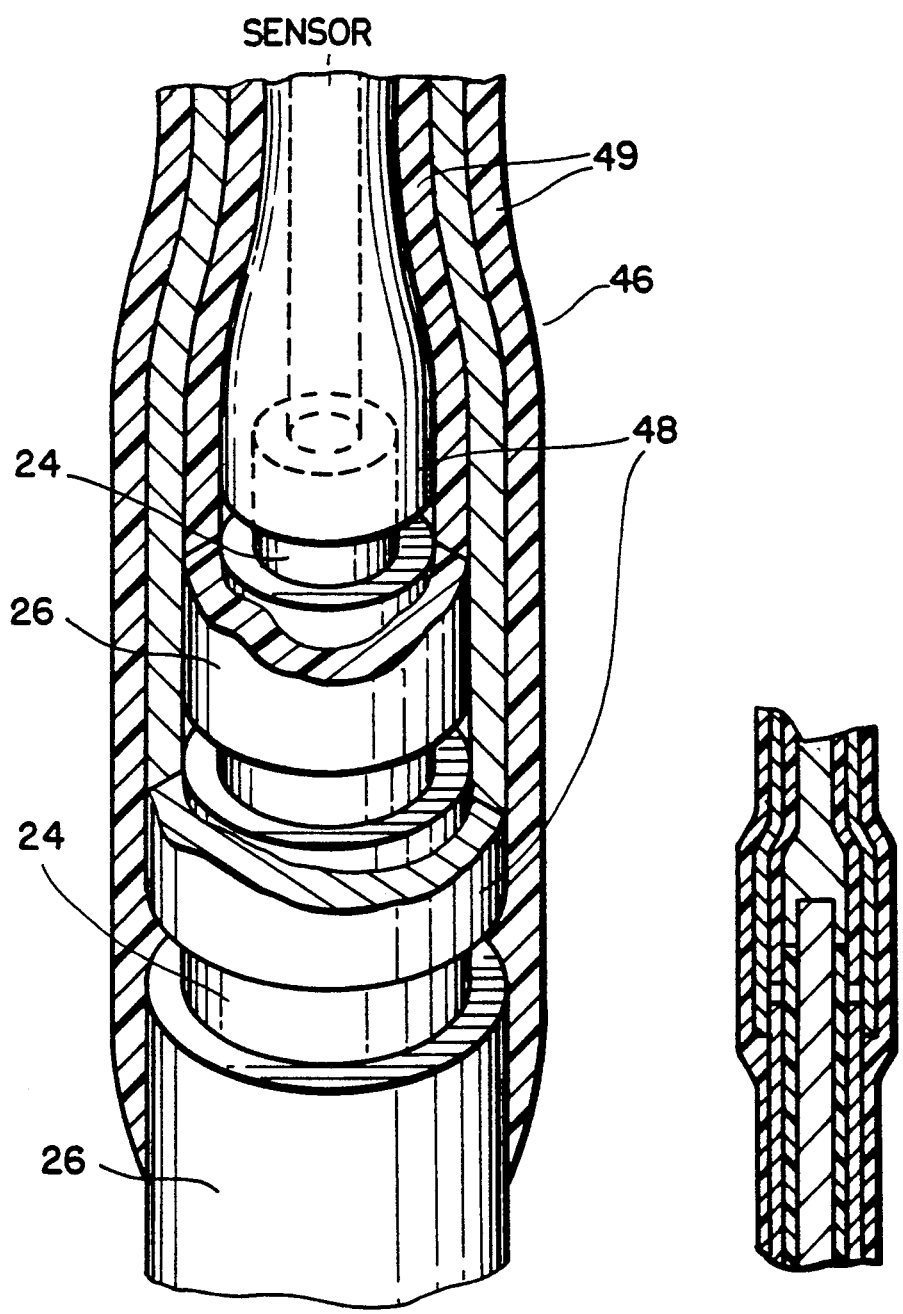
FIGS. 10 and 10A are perspective and cross-sectional views of the electrode lead of FIG. 3 in which connection is made by overlapping the conductors.

FIGS. 10 and 10A illustrate another structure for connecting a sensor to the alternative embodiment of FIG. 3(a). The connector 46 has an internally stepped receiving tip with conductive concentric rings that form conductor sockets 48 and insulating material encasing the conductive rings that form connector insulating layers 49. Sockets 48 couple with respective coaxial conductors 24 on the stepped distal end of the electrode lead 12 in a plug-and-jack manner. Receiving tip insulator layers 49 couple with respective insulator layers on the stepped distal end of the electrode lead 12. The connector 46, for example, may be comprised of deep drawn metal "flared" cylinders which in certain situations may be the receiving portion of a pulse generator.

Figure 11:
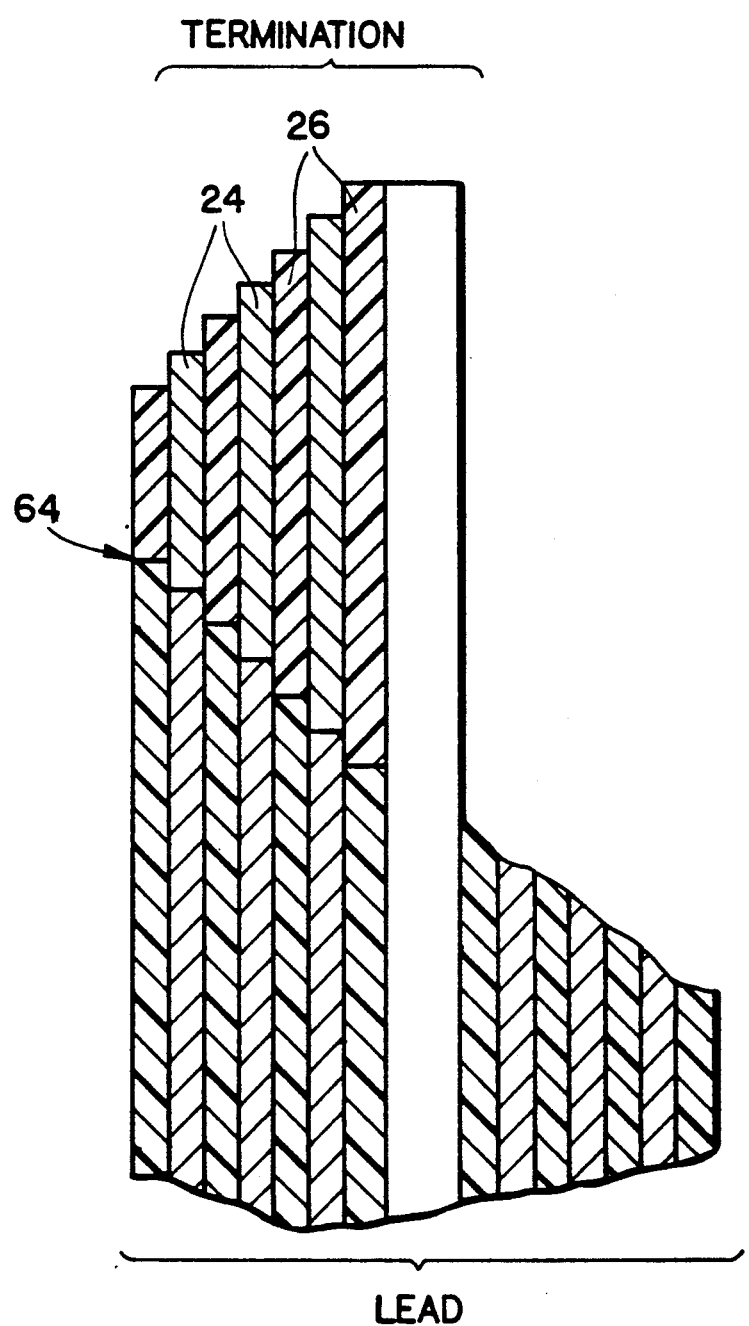
FIG. 11 is a side sectional view of the proximal end of the electrode lead of FIG. 3 in which connection is made by a butt joint aided by conductive adhesive.

In accordance with the present invention, the distal end of the electrical conductor may be stripped of insulation and stepped at predetermined intervals to fit a respective proximal end of another electrode lead to form a conductive butt joint. As embodied herein, either end of a coaxial-type conductive lead 12 may be terminated with a butt joint 64 as illustrated in FIG. 11.

The butt joint is formed by inwardly stepping the female end of one electrode lead and outwarding stepping the male end of another electrode lead such that the male end mechanically plugs into the female end to form the butt joint 64. The joint may be further secured by use of a conductive adhesive between the joining members. Any number of electrode leads may be joined to other electrode leads that include the above butt joint ends.

Figure 12:
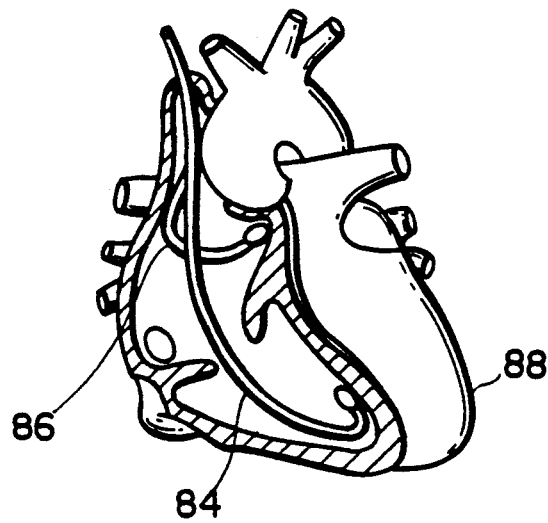
FIG. 12 is a perspective view, in partial cross-section, of the heart muscle depicting an endocardial cardioversion system employing a J-shaped atrial endocardial lead and a J-shaped ventricular endocardial lead in accordance with another embodiment of the present invention.

Referring to FIG. 12, there is shown a preferred embodiment of an endocardial lead system. In this embodiment a ventricular J-shaped electrode 84 is used in combination with a J-shaped atrial electrode 86 in the heart 88. The J-shaped bends provide increased length over which the electrodes may be mounted, resulting in large surface area electrodes on thinner, more flexible leads, which can be used with reduced risk of perforation of the endocardium. The J-shaped ventricular lead reduces the risk of perforation further by allowing the force applied by the lead to the apex of the right ventricle to be distributed over a greater area.

Figure 13:
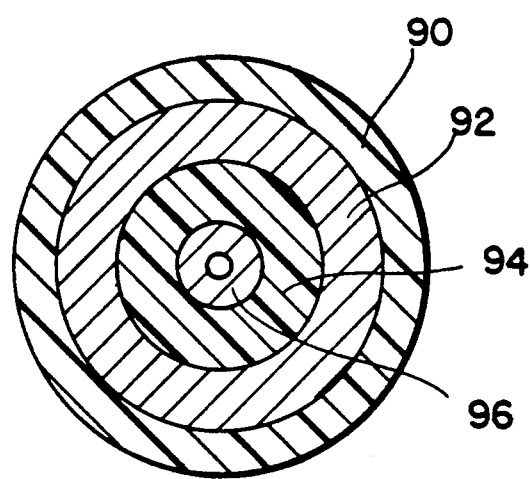
FIG. 13 is a cross-sectional view of a first embodiment of an electrode lead suitable for the endocardial system illustrated in FIG. 12.

Referring to FIG. 13, there is shown a cross-section of the RV electrode of the transvenous cardioversion lead system of FIG. 12. Helical metal conductors 92 and 96 are mounted coaxially within the lead. The two conductors are mutually insulated by a polyurethane sheath 94. Outer sheath 90, which acts as a conductor while protecting the heart tissue from damage, is preferably formed from a conductive, inert, biocompatible material such as carbon fibers or a polymer.

Sheath 90 may take the form of a tube with a smooth non-abrasive surface, or a helical wrapping of a filamentary conductive non-abrasive polymer material. In the case of a helical wrapping, the cross-sectional shape and area of the filament are selected so as to eliminate the existence of ridges and indentations which produce abrasive effects on cardiac tissue, which as discussed hereinabove can produce tissue damage or thrombogenesis.

Suitable polymers for this embodiment are the same as those disclosed herein for the embodiments of FIGS. 1-11. The polymer materials are able to supply a cardioverting/defibrillating energy discharge having a magnitude of up to 40 Joules or more.

Alternatively, conducting polymers can be created by thin film deposition of metal onto a polymer such as the coating of polyamide with platinum or the metal plating of microporous polytetralfluoroethylene (PTFE) as disclosed in U.S. Pat. No. 4,557,957 to Manniso entitled "Microporous Metal-Plated Polytetrafluoroethylene Articles and Method of Manufacture." Suitable metals for plating PTFE include nickel, silver, gold and platinum.

Figure 14:
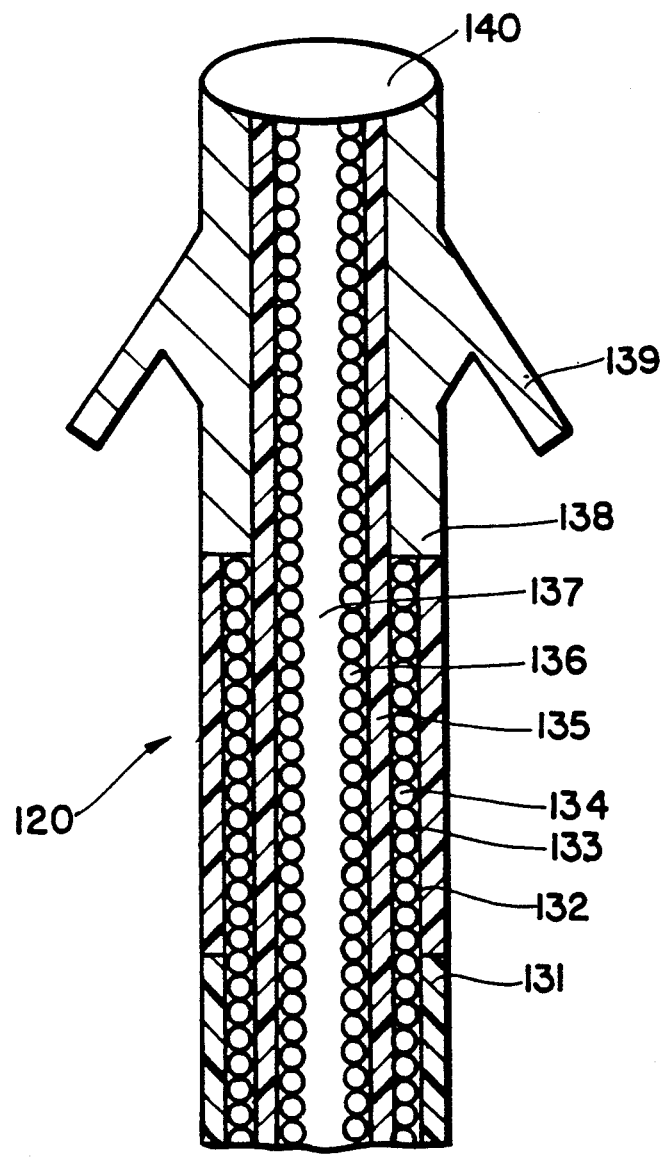
FIG. 14 is a fragmentary sectional view of another embodiment of an electrode lead.

Referring to FIG. 14, there is shown a fragmentary sectional view of an implantable sensing and stimulating bipolar lead 120 in accordance with another embodiment of the present invention. Lead 120 comprises a central axial passage 137 within which is disposed a helical conductor 136 extending at one end toward the distal electrode 140 and at the other to a terminal which establishes an electrical connection between the sensing and stimulating device and the distal tip region.

An insulating sheath 135, extending toward distal electrode 140, is disposed coaxially within lead 120 between the inner helical conductor 136 and an outer helical conductor 134. The outer helical conductor 134 is surrounded by a porous polymer sheath 132 which, in the region 131 extending from the proximal end of the lead 120 to a proximal electrode 133, has its pores filled with a non-conductive polymer and hence is insulative. In the region 132 of the proximal electrode 133, the porous polymer sheath is conductive due to the infusion of a conductive substance into the pores. An insulation body 138 with tine molding 139 for anchoring the lead 120 within the heart, extends from the distal end of the proximal electrode 133 to the distal tip region 140 of the lead 120.

The porous polymer sheath may be formed from a substrate such as polyurethane, Teflon or Dacron (which are both registered trademarks), or other plastic material, platinum, titanium or other metal as well as carbon and ceramic materials, which has undergone a technique such as laser drilling or sintering in order to become porous. The conductive substance which infuses the pores of the polymer may be formed from body fluids, a conductive gel, or a layer of poly (2-hyroxyethylmethacrylate) (polyHEMA) or Nafion, which is the registered trademark for perfluorosulphonic acid. Suitable materials for the insulation sheaths 135 and 138 and the tine molding 139 include silicone rubber or polyurethane.

One particular advantage of the lead 120 is that fibrous ingrowth may occur in the porous portion of the lead, thus securing the lead to the heart wall and further reducing the risk of damage caused by movement of the lead within the heart. The lead is also thin and flexible.

Although the electrode lead desribed herein is a cardioversion lead, the lead of the invention may be used in connection with other types of electrotherapy to the heart, including pacing.

In view of the foregoing, the present invention involves a body implantable electrode lead apparatus utilizing conductive polymers. The electrode leads of the invention do not suffer from corrosion or fatigue problems associated with traditional body implantable electrode leads. The invention disclosed may be produced with an integral stimulating tip or sensor that requires less space than traditional electrode lead connections. Electrode leads according to the invention are highly flexible and are capable of incorporating multipolar conductors. This electrode lead will offer designers of biomedical devices great design flexibility at a reasonable cost.

It will be apparent to those skilled in the art that modifications and variations can be made in the electrode lead apparatus of this invention. The invention in its broader aspects is, therefore, not limited to the specific details, representative methods and apparatus, and illustrative examples shown and described hereinabove. Thus, it is intended that all matter contained in the foregoing description or shown in the accompanying drawings shall be interpreted as illustrative and not in a limiting sense.

What is claimed is:

1. A flexible electrode cardioversion or defibrillation lead for use in a transvenous lead system for supplying electrotherapy to the heart comprising:
    an inner conductive layer;
    an insulative layer surrounding said inner conductive layer;
    an outer conductive layer surrounding said insulative layer; and
    an outer conductive sheath surrounding at least a portion of said outer conductive layer;
    wherein said sheath is formed from a flexible, biocompatible material having a non-abrasive effect on cardiac tissue during operation of said lead, said material comprising intrinsically conducting polymers, said material being able to supply a cardioverting/defibrillating energy discharge having a magnitude of up to 40 Joules.

2. The lead of claim 1, wherein said conducting polymers are selected from the group consisting of polyacetylene, polypyrolle, poly (para-phenylene), poly (para-phenylene sulfide), poly (sulfur nitride) and polymers wherein electrical conductivity is increased by doping.

* * * * *